United States Patent
Nielsen et al.

(10) Patent No.: US 9,181,248 B2
(45) Date of Patent: *Nov. 10, 2015

(54) [1,2,4]TRIAZOLOPYRIDINES AND THEIR USE AS PHOSPHODIESTERASE INHIBITORS

(71) Applicant: LEO Pharma A/S, Ballerup (DK)

(72) Inventors: Simon Feldbaek Nielsen, Ballerup (DK); Jens Christian Hojland Larsen, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/572,218

(22) Filed: Dec. 16, 2014

(65) Prior Publication Data
US 2015/0105420 A1    Apr. 16, 2015

Related U.S. Application Data

(62) Division of application No. 14/361,356, filed as application No. PCT/EP2012/076191 on Dec. 19, 2012, now Pat. No. 8,940,761.

(60) Provisional application No. 61/578,677, filed on Dec. 21, 2011, provisional application No. 61/666,430, filed on Jun. 29, 2012.

(51) Int. Cl.
*A61K 31/437* (2006.01)
*C07D 471/04* (2006.01)

(52) U.S. Cl.
CPC ............ *C07D 471/04* (2013.01); *A61K 31/437* (2013.01)

(58) Field of Classification Search
USPC .......................................... 514/303, 861, 863
See application file for complete search history.

(56) References Cited

FOREIGN PATENT DOCUMENTS

| EP | 0771794 A1 | 5/1997 |
|---|---|---|
| EP | 0943613 A1 | 9/1999 |
| WO | WO 2008/125111 A1 | 10/2008 |
| WO | WO 2010/069322 A1 | 6/2010 |

OTHER PUBLICATIONS

Brian J. Lipworth "Phosphodiesterase-4 inhibitors for asthma and chronic obstructive pulmonary disease", Lancet 2005, vol. 365, pp. 167-175.
Card et al. "Structural Basis for the Activity of Drugs that Inhibit Phosphodiesterases", Structure, vol. 12, Dec. 2004, pp. 2233-2247.
Holden et al. "Monocyte Localization of Elevated cAMP Phosphodiesterase Activity in Atopic Dermatitis", The Journal of Investigative Dermatology (1986), vol. 87, No. 3, pp. 372-376.
Houslay et al. "Phosphodiesterase-4-selective inhibitors have therapeutic potential for treating major diseases such as asthma and chronic obstructive pulmonary disease, as well as depression, Parkinson's disease and Alzheimer's disease", Drug Discovery Today, vol. 10, No. 22, Nov. 2005, pp. 1503-1519.
Huang et al. " Phosphodiesterase 4 Inhibitors for the Treatment of Asthma and COPD", Current Medicinal Chemistry, 2006, vol. 13, No. 27, pp. 3253-3262.
International Search Report, issued in PCT/EP2012/076191, dated Apr. 5, 2013.
Kroegel et al. "Phosphodiesterase-4 inhibitors as a novel approach for the treatment of respiratory disease: cilomilast", Expert Opinion Investigational Drugs 2007, vol. 16, No. 1, pp. 109-124.
Smith et al. "Selective phosphodiesterase 4 inhibitors in the treatment of allergy and inflammation", Current Opinion in Investigational Drugs 2005, vol. 6, No. 11, pp. 1136-1141.
Written Opinion of the International Search Authority, issued in PCT/EP2012/076191, dated Apr. 5, 2013.

*Primary Examiner* — Charanjit Aulakh
(74) *Attorney, Agent, or Firm* — Birch Stewart Kolasch & Birch, LLP

(57) ABSTRACT

The present invention relates to novel [1,2,4]triazolopyridine compounds with phosphodiesterase inhibitory activity, as well as to their use as therapeutic agents in the treatment of inflammatory diseases and conditions.

1 Claim, No Drawings

[1,2,4]TRIAZOLOPYRIDINES AND THEIR USE AS PHOSPHODIESTERASE INHIBITORS

CROSS REFERENCE

The present application is a 37 C.F.R. §1.53(b) divisional of, and claims priority to, U.S. application Ser. No. 14/361,356, filed May 29, 2014. Application Ser. No. 14/361,356 is the national phase under 35 U.S.C. §371 of International Application No. PCT/EP2012/076191, filed on Dec. 19, 2012. Priority is also claimed to U.S. Provisional Application 61/578,677 filed on Dec. 21, 2011 and U.S. Provisional Application 61/666,430 filed on Jun. 29, 2012. The entire contents of each of these applications are hereby incorporated by reference.

FIELD OF THE INVENTION

The present invention relates to novel [1,2,4]triazolopyridine compounds with phosphodiesterase inhibitory activity, as well as to their use as therapeutic agents in the treatment of inflammatory diseases and conditions.

BACKGROUND OF THE INVENTION

Phosphodiesterases are enzymes that catalyse the hydrolysis of cyclic AMP and/or cyclic GMP in cells to 5-AMP and 5-GMP, respectively, and as such they are critical to cellular regulation of cAMP or cGMP levels. Of the 11 phosphodiesterases identified so far, phosphodiesterase (PDE) 4, PDE7 and PDE8 are selective for cAMP. PDE4 is the most important modulator of cAMP expressed in immune and inflammatory cells such as neutrophils, macrophages and T-lymphocytes (Z. Huang and J. A. Mancini, Current Med. Chem. 13, 2006, pp. 3253-3262). As cAMP is a key second messenger in the modulation of inflammatory responses, PDE4 has been found to regulate inflammatory responses of inflammatory cells by modulating proinflammatory cytokines such as TNF-α, IL-2, IFN-γ, GM-CSF and LTB4. Inhibition of PDE4 has therefore become an attractive target for the therapy of inflammatory diseases such as asthma, chronic obstructive pulmonary disease (COPD), rheumatoid arthritis, atopic dermatitis, inflammatory bowel disease such as Crohn's disease etc. (M. D. Houslay et al., Drug Discovery Today 10 (22), 2005, pp. 1503-1519). As atopic dermatitis (AD) patients have increased PDE-activity, PDE4-inhibition would also appear to be a viable treatment of AD (Journal of Investigative Dermatology (1986), 87(3), 372-6).

The PDE4 gene family consists at least of four genes, A, B, C and D, which have a high degree of homology (V. Boswell Smith and D. Spina, Curr. Opinion Investig. Drugs 6(11), 2006, pp. 1136-1141). The four PDE4 isoforms are differentially expressed in different tissues and cell types. Thus, PDE4B is predominantly expressed in monocytes and neutrophils, but not in cortex and epithelial cells, while PDE4D is expressed in lung, cortex, cerebellum and T-cells (C. Kroegel and M. Foerster, Exp. Opinion Investig. Drugs 16(1), 2007, pp. 109-124). It has been speculated that inhibition of PDE4D in the brain is associated with the adverse effects found when administering PDE4 inhibitors clinically, primarily nausea and emesis, whereas inhibition of PDE4B is associated with anti-inflammatory effects (B. Lipworth, Lancet 365, 2005, pp. 167-175). However, the PDE inhibitors developed so far are not believed to be specific for any of the four PDE4 isoforms.

Numerous PDE4 inhibitors have been studied for their therapeutic effect on inflammatory diseases, primarily asthma and COPD.

The first of these, theophylline, is a weak, non-selective phosphodiesterase inhibitor used in the treatment of respiratory diseases such as asthma and COPD. Treatment with theophylline may, however, give rise to both mild and severe adverse effects, e.g. arrhythmia and convulsions, restricting the clinical utility of theophylline (Kroegel and Foerster, supra). As phosphodiesterase has remained an attractive target for anti-inflammatory therapy, several other, more selective PDE4 inhibitors have been developed and investigated in a clinical setting. The clinical development of many of the first-generation PDE4 inhibitors such as rolipram was discontinued due to dose-limiting side effects, primarily nausea and emesis. However, Roflumilast was approved in 2010 for severe COPD associated with chronic bronchitis after dose-limiting side effects, nausea, diarrhea and headache were minimized. Second-generation PDE4 inhibitors with apparently less pronounced adverse effects are currently in clinical trials (Houslay, supra). PDE4 inhibitors are for example disclosed in EP 0771794 and EP 0943613.

WO 2008/125111, LEO Pharma A/S, discloses triazolopyridine compounds with a potent PDE4 inhibiting activity. These compounds include a linker including a carbonyl group between a bicyclic, heterocyclic ring system and a monocyclic ring system. It has been shown for a related compound, piclamilast, that the linker is extremely important for the positioning of the monocyclic ring such that it may interact with the PDE4 enzyme (Card G. L., et al, "Structural basis for the activity of drugs that inhibit phosphodiesterases", Structure 2004 December; 12(12); 2233-47) to give the desired inhibitory effect.

WO 2010/069322, LEO Pharma A/S, discloses triazolopyridine compounds, without a carbonyl linker between the bicyclic and the monocyclic ring system. The compounds have been found to exhibit PDE4 inhibitory activity.

There is a continued need for developing novel PDE4 inhibitors which have a more favourable therapeutic window, i.e. fewer adverse effects, while retaining their therapeutic anti-inflammatory effect.

SUMMARY OF THE INVENTION

It is an object of the present invention to provide novel compounds which are potent PDE4 inhibitors having a stability profile in biological tissue that implies that only a very low systemic exposure of the compounds will be observed upon e.g. topical administration. More precisely the compounds of the present invention have high clearance in human liver microsomes. They rapidly hydrolyse in human whole blood but do at the same time display stability towards enzymatic hydrolyses in human keratinocytes.

In one aspect the invention provides a compound of Formula (I)

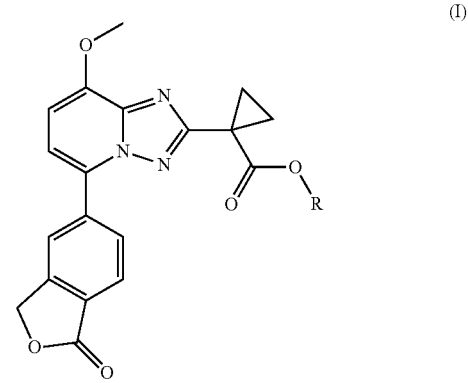

(I)

wherein R is as defined below.

In another aspect, the invention provides pharmaceutical compositions comprising a compound of general formula (I) as defined above together with a pharmaceutically acceptable vehicle or excipient or pharmaceutically acceptable carrier(s), optionally together with one or more other therapeutically active compound(s).

In another aspect, the invention provides the use of a compound of the invention, for the manufacture of pharmaceutical compositions for the prophylaxis, treatment, prevention or amelioration of a disease, disorder or condition responsive to PDE4 inhibitory activity.

In yet another aspect the invention provides a method for prophylaxis, treatment, prevention or alleviation of diseases, disorders or conditions responsive to PDE4 inhibitory activity, and which method comprises the step of administering to a living animal body a therapeutically effective amount of the compound of formula (I) of the invention.

Other objects of the invention will be apparent to the person skilled in the art from the following detailed description and examples.

DETAILED DESCRIPTION OF THE INVENTION

In one aspect the invention provides a compound of Formula (I)

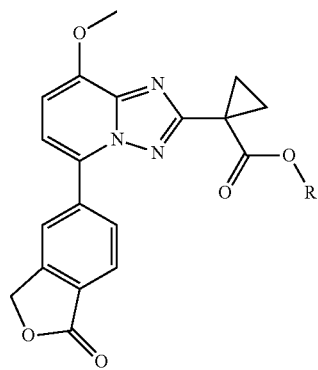

any of its stereoisomers or any mixture of its stereoisomers or a pharmaceutically acceptable salt thereof,
wherein R is branched butyl.

In one embodiment of the present invention, R is 1-methylpropyl, 2-methylpropyl or tert-butyl.

In another embodiment R is 1-methylpropyl.
In another embodiment R is 2-methylpropyl.
In another embodiment R is tert-butyl.

Specific examples of compounds of formula (I) may be selected from the group consisting of:

[(1S)-1-Methylpropyl]1-[8-methoxy-5-(1-oxo-3H-isobenzofuran-5-yl)-[1,2,4]triazolo-[1,5-a]pyridin-2-yl]cyclopropanecarboxylate;

[(1R)-1-Methylpropyl]1-[8-methoxy-5-(1-oxo-3H-isobenzofuran-5-yl)-[1,2,4]triazolo[1,5-a]pyridin-2-yl]cyclopropanecarboxylate;

[2-Methylpropyl]1-[8-methoxy-5-(1-oxo-3H-isobenzofuran-5-yl)-[1,2,4]triazolo[1,5-a]pyridin-2-yl]cyclopropanecarboxylate;

Tert-butyl 1-[8-methoxy-5-(1-oxo-3H-isobenzofuran-5-yl)-[1,2,4]triazolo[1,5-a]pyridin-2-yl]cyclopropanecarboxylate; or a pharmaceutically acceptable salt thereof.

DEFINITIONS

As used throughout the present specification and appended claims, the following terms have the indicated meaning:

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "pharmaceutically acceptable" as used herein means suited for normal pharmaceutical applications, i.e. giving rise to no adverse events in patients etc.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid.

The compounds of the invention may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula (I) may or may not comprise asymmetrically substituted (chiral) carbon atoms which give rise to the existence of isomeric forms, e.g. enantiomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Said pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials.

Medical Use

As the compounds of the invention exhibit PDE4 inhibitory activity, the compounds may be useful as therapeutic agents for inflammatory allergic diseases such as bronchial asthma, COPD, allergic rhinitis, and nephritis; autoimmune diseases such as rheumatoid arthritis, multiple sclerosis, Crohn's disease, and systemic lupus erythematosus; acute or chronic cutaneous wound disorders; diseases of the central nervous system such as depression, amnesia, and dementia; organopathy associated with ischemic reflux caused by cardiac failure, shock, and cerebrovascular diseases, and the like; insulin-resistant diabetes; wounds; AIDS, and the like.

In one embodiment, the compounds of the present invention are considered useful for the treatment, prevention or alleviation of dermal diseases or conditions.

In another embodiment, the compounds of the present invention are considered useful for the treatment, prevention or alleviation of dermal diseases or conditions selected from the group consisting of proliferative and inflammatory skin disorders, dermatitis, atopic dermatitis, seborrheic dermatitis, contact dermatitis, psoriasis, cancer, epidermal inflammation, alopecia, skin atrophy, steroid induced skin atrophy, skin ageing, photo skin ageing, acne, urticaria, pruritis, and eczema.

In another embodiment, the compounds of the present invention are considered useful for the treatment or alleviation of atopic dermatitis.

In another embodiment, the compounds of the present invention are considered useful for the treatment or alleviation of psoriasis.

Compounds of the invention, optionally in combination with other active compounds, may be useful for the treatment of dermal diseases or conditions, in particular for the treatment of proliferative and inflammatory skin disorders, dermatitis, atopic dermatitis, seborrheic dermatitis, contact dermatitis, psoriasis, cancer, epidermal inflammation, alopecia, skin atrophy, steroid induced skin atrophy, skin ageing, photo skin ageing, acne, urticaria, pruritis, and eczema.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition. The invention therefore relates to a pharmaceutical composition comprising a compound of formula (I), optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

In the form of a dosage unit, the compound may be administered one or more times a day at appropriate intervals, always depending, however, on the condition of the patient, and in accordance with the prescription made by the medical practitioner. Conveniently, a dosage unit of a topical formulation contain between 0.1 mg and 1000 mg, preferably between 1 mg and 100 mg, such as 5-50 mg of a compound of formula (I).

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.001 to 10 mg/kg body weight, e.g. in the range from 0.01 to 1 mg/kg body weight. The compound may be administered as a bolus (i.e. the entire daily doses is administered at once) or in divided doses two or more times a day.

In the context of topical treatment it may be more appropriate to refer to a "usage unit", which denotes unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. A "usage unit" is capable of being administered topically to a patient in an application per square centimeter of the skin of from 0.1 mg to 50 mg and preferably from 0.2 mg to 5 mg of the final formulation in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics*, $9^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramus-cular, intraarticular and intravenous), transdermal, ophthalmic, topical, dermal, nasal or buccal administration. Topical administration of the claimed formulation is particularly suitable.

The formulations may conveniently be presented in dosage unit form and may be prepared by any of the methods well known in the art of pharmacy, e.g. as disclosed in Remington, *The Science and Practice of Pharmacy*, $20^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula (I) may be presented as a sterile, solid preparation, e.g. a freeze-dried powder, which is readily dissolved in a sterile solvent immediately prior to use.

Transdermal formulations may be in the form of a plaster or a patch.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin.

For topical administration, the compound of formula (I) may typically be present in an amount of from 0.01 to 5% by weight of the composition, e.g. from 0.01% to 1% by weight of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula (I) may include one or more additional ingredients such as diluents, buffers, flavouring agents, colourant, surface active agents, thickeners, preservatives, e.g. methyl hydroxybenzoate (including anti-oxidants), emulsifying agents and the like.

The pharmaceutical composition may additionally comprise one or more other active components conventionally used in the treatment of dermal disease or conditions, e.g. selected from the group consisting of glucocorticoids, vitamin D and vitamin D analogues, antihistamines, platelet activating factor (PAF) antagonists, anticholinergic agents, methylxanthines, β-adrenergic agents, COX-2 inhibitors, salicylates, indo-methacin, flufenamate, naproxen, timegadine, gold salts, penicillamine, serum cholesterol lowering agents, retinoids, zinc salts, salicylazosulfapyridine and calcineurin inhibitors.

Methods of Preparation

The compounds of the present invention can be prepared in a number of ways well known to those skilled in the art of synthesis. The compounds of formula (I) may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials are either known or commercially available compounds or can be prepared by routine synthetic methods well known to a person skilled in the art.

LCMS Method "XE Metode 7 CM"

A quality check was performed on a Waters LCT Premier MS instrument and a Waters Aquity UPLC.

Column: Waters Aquity UPLC HSS T3 1.8 µm, 2.1×50 mm, at 40° C.

Solvents: A=10 mM ammonium acetate+0.1% HCOOH, B=MeCN+0.1% HCOOH.

Flow: 0.7 ml/min. Injection volume 2 µl. UV detection range 240-400 nm.

|  | Time | % A | % B |
| --- | --- | --- | --- |
| Gradient: | 0.00 min | 99 | 1 |
|  | 0.50 min | 94 | 6 |
|  | 1.00 min | 94 | 6 |
|  | 2.60 min | 5 | 95 |
|  | 3.80 min | 5 | 95 |
|  | 3.81 min | 99 | 1 |
|  | 4.80 min | 99 | 1 |

The MW confirmation and purity was extracted and checked with OpenLynx.

$^1$H Nuclear magnetic resonance (NMR) spectra were recorded at 400 or 600 MHz. Chemical shift values (δ, in ppm) are quoted in the specified solvent relative to internal tetramethylsilane (δ=0.00) or chloroform (δ=7.25) standards. The value of a multiplet, either defined (doublet (d), triplet (t), quartet (q)) or not (m) at the approximate midpoint is given unless a range is quoted. (bs) indicates a broad singlet. The organic solvents used were usually anhydrous. Chromatography was performed on Merck silica gel 60 (0.040-0-063 mm). The solvent ratios indicated refer to v:v unless otherwise noted.

The following abbreviations have been used throughout:
DBU 1,8-diazabicyclo[5.4.0]undec-7-ene
DCE 1,2-dichloroethane DCM dichloromethane
DIAD diisopropyl azodicarboxylate
DMAP N,N-dimethylpyridin-4-amine
DMF N,N-dimethylformamide
DMSO dimethylsulfoxide
EDCI (3-dimethylamino-propyl)-ethyl-carbodiimide
EtOH ethanol
MeOH methanol
EtOAc ethyl acetate
L liter Me methyl
NMR nuclear magnetic resonance
RT room temperature
THF tetrahydrofuran
Pet. petroleum General Methods The compounds of the invention may for example be prepared according to the following non-limiting general methods and examples. R is as previously defined for the compounds of Formula (I):

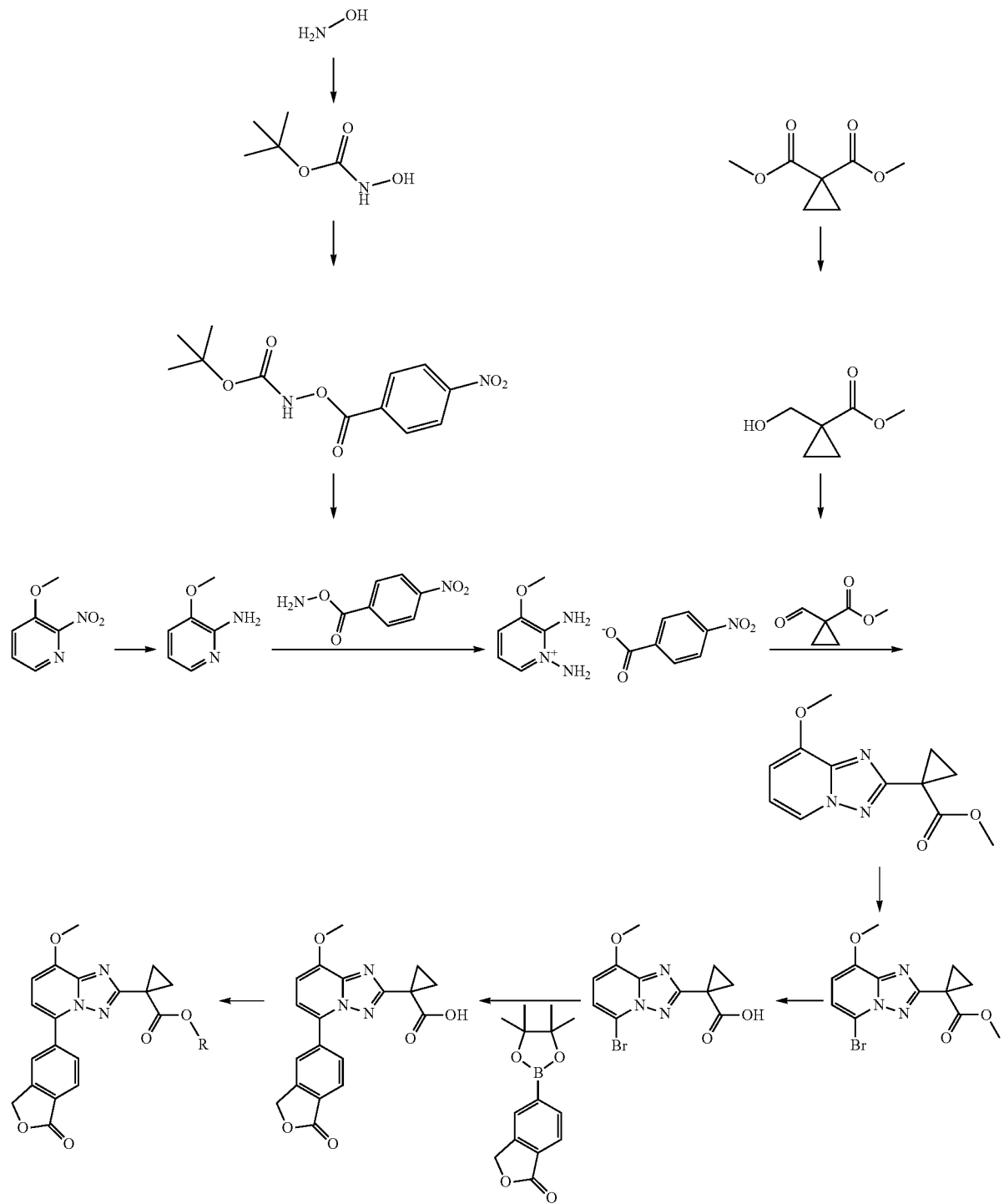

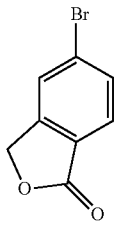

Preparation 1

Tert-Butyl hydroxycarbamate

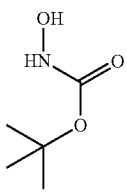

To a stirred suspension of hydroxylamine.HCl (150 g, 2.17 mol) and K₂CO₃ (150 g, 1.09 mol) in diethyl ether (940 mL) and water (30 mL) at 0° C., a solution of di-tert-butyl dicarbonate (308 g, 1.41 mmol) in diethyl ether (600 mL) was added slowly for 15 min. After addition the reaction mixture was stirred at RT for 2 hours. The reaction mixture was filtered and the filtrate was dried over anhydrous Na₂SO₄ and concentrated. The obtained crude was washed with cyclohexane (50 mL×3) and dried to afford the title compound (150 g, 52%, white solid). ¹H NMR (400 MHz, CDCl₃): δ=7.18 (br, 2H), 1.47 (s, 9H) ppm.

Preparation 2

Tert-Butyl 4-nitrobenzoyloxycarbamate

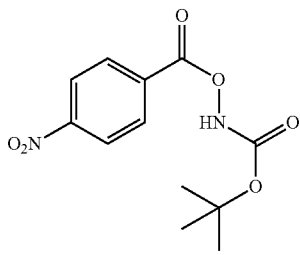 [SMILES: CC(C)(C)OC(=O)NOC(=O)c1ccc([N+](=O)[O-])cc1]

To a stirred solution of tert-butyl hydroxyl carbamate (150 g, 1.128 mol) in dichloromethane (2 L) at 0° C., triethylamine (174 mL, 1.24 mol) was added followed by 4-nitrobenzoyl chloride (205 g, 1.105 mol) in equal portions. After the addition was completed the reaction mixture was stirred at RT for 1 hour. The reaction mixture was quenched with water (500 mL) and extracted. The separated dichloromethane layer was washed with brine (200 mL), dried over anhydrous Na₂SO₄ and concentrated. The obtained crude was washed with hexane (100 mL×2) and dried to afford the title compound (300 g, 94%, yellow solid). ¹H NMR (400 MHz, CDCl₃): δ=8.34-8.27 (m, 4H), 2.97-2.92 (m, 1H), 1.53 (s, 9H) ppm.

Preparation 3

O-(4-Nitrobenzoyl)hydroxylamine

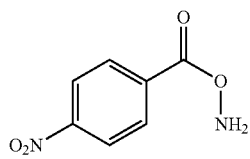 [SMILES: NOC(=O)c1ccc([N+](=O)[O-])cc1]

To a stirred solution of tert-butyl 4-nitrobenzoyloxy carbamate (300 g, 1.06 mol) in dichloromethane (2 L) at 0° C., methanesulphonic acid (69 mL, 1.06 mol) was added slowly. After the addition was completed, the reaction mixture was allowed to stir at RT for 16 hours. The reaction mixture was diluted with dichloromethane (1 L), washed with 10% aq NaHCO₃ (300 mL), water (200 mL), brine (200 mL), dried over anhydrous Na₂SO₄ and concentrated. The obtained crude was washed with hexane (100 mL×2) and dried to afford the title compound (150 g, 77%, pale yellow solid). ¹H NMR (400 MHz, CDCl₃): δ=8.33-8.30 (m, 2H), 8.22-8.19 (m, 2H), 6.73 (brs, 2H) ppm.

Preparation 4

1-Hydroxmethyl-cyclopropanecarboxylic acid ethyl ester

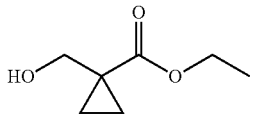

To a stirred solution of diethyl cyclopropane-1,1-dicarboxylate (2.13 g, 11.4 mmol) in THF (80 mL) at RT, lithium aluminum tri-tert-butoxyhydride (38.76 mL, 38.76 mmol, 1.0 M solution in THF) was added slowly. After the addition was completed, the reaction mixture was stirred at RT for 18 hours. The reaction mixture was diluted with ethyl acetate (100 mL), washed with 1N aq HCl (20 mL), water (20 mL), 5% aq. NaHCO₃ (25 mL), brine (20 mL), dried over anhydrous Na₂SO₄, filtered and concentrated to afford the title compound (1.3 g, 79%, yellow oil). ¹H NMR (400 MHz, CDCl₃): δ=4.20-4.13 (m, 2H), 3.62 (m, 2H), 2.61 (m, 1H), 1.29-1.24 (m, 5H), 0.88-0.85 (m, 2H) ppm.

Preparation 5

1-Formyl-cyclopropanecarboxylic acid ethyl ester

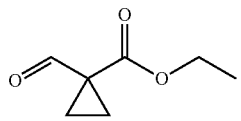

To a stirred solution of 1-hydroxmethyl-cyclopropanecarboxylic acid ethyl ester (1.1 g, 7.63 mmol) in dichloromethane (45 mL), NaHCO₃ (2.5 g, 29.76 mmol) and Dess-Martin periodinane (6.46 g, 15.23 mmol) were added. The suspension was then stirred at RT for 30 min. The reaction mixture was quenched with a 1:1 solution of 10% aq. Na₂S₂O₃ and 10% aq. NaHCO₃ (20 mL) maintain the temperature below 20° C., stirred for 30 min. The reaction mixture was then diluted with dichloromethane (100 mL) and extracted. The organic layer was washed with brine (30 mL), dried over anhydrous Na₂SO₄, filtered and concentrated. The crude was purified by silica gel column chromatography (0 to 10% EtOAc in pet. ether as eluent) to afford the title compound (800 mg, 76%, yellow oil). ¹H NMR (400 MHz, CDCl₃): δ=10.40 (s, 1H), 4.25 (m, 2H), 1.68-1.65 (m, 2H), 1.62-1.59 (m, 2H), 1.33-1.26 (m, 3H) ppm.

Preparation 6

3-Methoxy-pyridin-2-ylamine

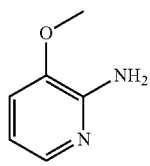

A suspension of 3-methoxy-2-nitropyridin (30 g, 194.8 mmol) and 10% Pd/C (10 g) in ethanol (1 L) was hydrogenated in a par hydrogenator (H₂, 40 psi pressure) at RT for 4 hours. The reaction mixture was filtered through celite and the filtrate was concentrated to afford the title compound (22 g, 91%, brown solid). ¹H NMR (400 MHz, CDCl₃): δ=7.66 (d, J=5.2 Hz; 1H), 6.91 (d, J=7.6 Hz, 1H), 6.63-6.60 (m, 1H), 4.65 (br, 2H), 3.84 (s, 3H) ppm.

Preparation 7

1,2-Diamino-3-methoxy-pyridinium salt of 4-nitrobenzoic acid

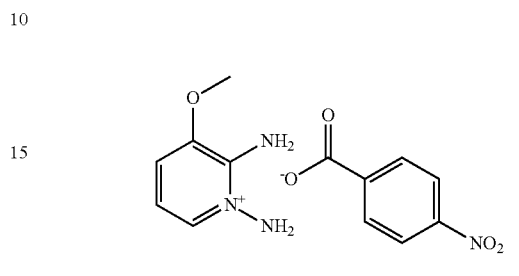

To a stirred solution of 3-methoxy-pyridin-2-ylamine (30 g, 164.8 mmol) in dichloromethane (400 mL), O-(4-nitrobenzoyl)hydroxylamine (13.2 g, 214.2 mmol) was added at 10° C. After addition the reaction mixture was stirred at RT for 16 hours. The resulted precipitate was filtered, washed with dichloromethane (25 mL×2) and dried to afford the title compound (40 g, 91%, brown solid) (CAUTION: The salt is thermally unstable). ¹H NMR (400 MHz, DMSO): δ=8.53 (br, 2H), 8.12 (d, J=8 Hz; 2H), 8.01 (d, J=8.8 Hz; 2H), 7.73 (d, J=6.4 Hz; 1H), 7.33 (d, J=7.2 Hz; 1H), 7.17 (br, 2H), 6.77 (t, J=6.8 Hz; 1H), 3.93 (s, 3H) ppm.

Preparation 8

1-(8-Methoxy-[1,2,4]triazolo[1,5-a]pyridine-2-yl)-cyclopropanecarboxylic acid ethyl ester

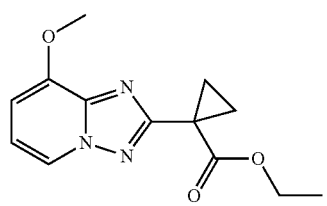 [SMILES: CCOC(=O)C1(c2nc3c(OC)cccn3n2)CC1]

To a stirred solution of diamino-3-methoxy-pyridinium salt of 4-nitrobenzoic acid (1 g, 7.14 mmol) in ethanol (10 mL) at 0° C., DBU (2.1 mL) was added followed by 1-formyl-cyclopropanecarboxylic acid ethyl ester (1.5 g, 10.71 mmol). After addition the reaction mixture was stirred at RT for 2 hours. The reaction mixture was concentrated, the obtained residue was diluted with EtOAc (100 mL), washed with water (20 mL×2), brine (20 mL), dried over anhydrous Na₂SO₄, filtered and concentrated. The crude was purified by silica gel column chromatography (using 0 to 15% EtOAc in CH₂Cl₂ as eluent) to afford the title compound (800 mg, 53%, white solid). ¹H NMR (400 MHz, CDCl₃): δ=8.18-8.16 (d, J=6.4 Hz; 1H), 6.89 (t, J=7.2 Hz, 1H), 6.76 (d, J=8 Hz; 1H), 4.20-

4.14 (m, 2H), 4.03 (s, 3H), 1.73-1.70 (m, 2H), 1.59-1.56 (m, 2H), 1.20 (t, J=6.8 Hz; 3H) ppm.

Preparation 9

1-(5-Bromo-8-methoxy-[1,2,4]triazolo[1,5-a]pyridin-2-yl)-cyclopropanecarboxylic acid ethyl ester

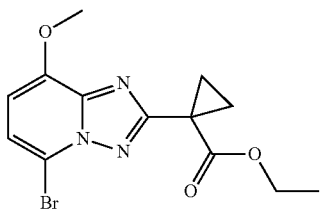 [SMILES: CCOC(=O)C1(c2nc3c(OC)ccc(Br)n3n2)CC1]

To a stirred solution of 1-(8-methoxy-[1,2,4]triazolo[1,5-a]pyridine-2-yl)-cyclopropanecarboxylic acid ethyl ester (25 g, 95.7 mmol) in acetonitrile (300 mL) at RT, N-bromosuccinimide (34 g, 191.5 mmol) was added portion wise. After addition the reaction mixture was stirred at RT for 6 hours. The reaction mixture was diluted with EtOAc (600 mL), washed with water (100 mL×2), brine (50 mL), dried over anhydrous Na$_2$SO$_4$, filtered and concentrated. The crude was purified by silica gel column chromatography (0 to 10% EtOAc in dichloromethane as eluent) to afford the title compound (25 g, 77%, colorless solid). $^1$H NMR (400 MHz, DMSO): δ=7.44 (d, J=8.4 Hz; 1H), 7.07 (d, J=8 Hz; 1H), 4.13-4.08 (m, 2H), 3.97 (s, 3H), 1.60-1.57 (m, 2H), 1.48-1.45 (m, 2H), 1.13 (t, J=7.4 Hz; 3H) ppm.

Preparation 10

1-(5-Bromo-8-methoxy-[1,2,4]triazolo[1,5-a]pyridin-2-yl)cyclopropanecarboxylic acid

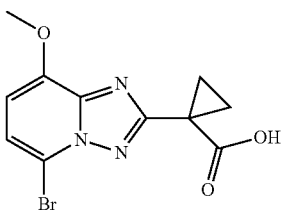 [SMILES: COc1ccc(Br)n2nc(C3(C(=O)O)CC3)nc12]

To a solution of ethyl 1-(5-bromo-8-methoxy-[1,2,4]triazolo[1,5-a]pyridin-2-yl)cyclopropanecarboxylate (3.00 g, 8.82 mmol) in THF (25 mL) was added an aqueous 1 M solution of LiOH (25 mL). The mixture was stirred at 80° C. for 30 minutes, cooled to room temperature and diluted with EtOAc (50 mL) and water (50 mL). The organic phase was extracted with an aqueous 0.1 M solution of NaOH (25 mL) and the combined aqueous phases were acidified with conc. HCl to pH 0-1, and extracted four times with DCM (30 mL). Evaporation to dryness of the combined organic phases yielded the title compound (2.54 g, 94%). $^1$H NMR (DMSO, 400 MHz): δ=12.61 (s, 1H), 7.42 (d, 1H, J=8.3 Hz), 7.06 (d, 1H, 3=8.3 Hz), 3.97 (s, 3H), 1.53 (q, 2H, 3=3.9 Hz), 1.40 (q, 2H, J=3.9 Hz) ppm.

Preparation 11

1-[8-Methoxy-5-(1-oxo-3H-isobenzofuran-5-yl)-[1,2,4]triazolo[1,5-a]pyridin-2-yl]cyclopropanecarboxylic acid

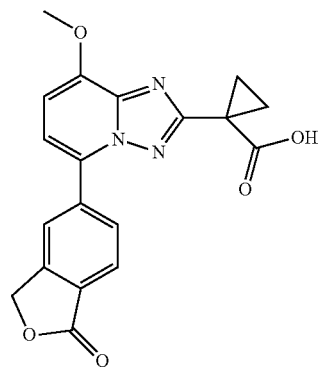 [SMILES: COc1ccc(-c2ccc3c(c2)COC3=O)n2nc(C3(C(=O)O)CC3)nc12]

1-(5-Bromo-8-methoxy-[1,2,4]triazolo[1,5-a]pyridin-2-yl)cyclopropanecarboxylic acid (1.00 g, 3.20 mmol) and 5-(4,4,5,5-tetramethyl-1,3,2-dioxaborolan-2-yl)-3H-isobenzofuran-1-one (preparation of the boronate was described in WO2011/134468) (1.67 g, 6.40 mmol) were dissolved in degassed dioxane (16 mL). Pd$_2$(dba)$_3$ (29 mg, 32 μmol), PCy$_3$ (18 mg, 64 μmol) and K$_3$PO$_4$ (2.38 g, 11.2 mmol) were mixed in degassed water (10 mL). The two solutions were mixed and subsequently heated in a micro wave oven to 110° C. for 10 minutes, cooled to room temperature and diluted with EtOAc (40 mL). The organic phase was extracted with water (25 mL) and an aqueous 0.1 M solution of NaOH (25 mL) and the combined aqueous phases were acidified with conc. HCl to pH 0-1, and extracted with DCM (30 mL×4). Upon evaporation of the combined organic phases the title compound crystallized out (746 mg, 64%). HPLC-Retention time (XE Metode 7 CM): 1.97 minutes. Detected "M+1"-mass: 366.11. Calculated "M+1"-mass: 366.11. $^1$H NMR (DMSO, 300 MHz): δ=8.25-8.20 (m, 1H), 8.13 (dd, 1H, J=8.2, 1.4 Hz), 8.00 (d, 1H, J=8.0 Hz), 7.40 (d, 1H, J=8.2 Hz), 7.24 (d, 1H, J=8.3 Hz), 5.51 (s, 2H), 4.04 (s, 3H), 1.58-1.48 (m, 2H), 1.48-1.39 (m, 2H) ppm.

Example 1

[(1S)-1-Methylpropyl]1-[8-methoxy-5-(1-oxo-3H-isobenzofuran-5-yl)-[1,2,4]triazolo-[1,5-a]pyridin-2-yl]cyclopropanecarboxylate (Compound 1)

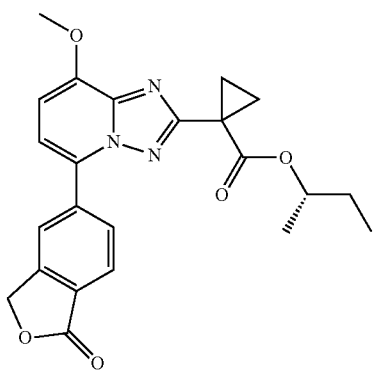 [SMILES: CC[C@H](C)OC(=O)C1(c2nc3c(OC)ccc(-c4ccc5c(c4)COC5=O)n3n2)CC1]

A mixture of 1-[8-methoxy-5-(1-oxo-3H-isobenzofuran-5-yl)-[1,2,4]triazolo[1,5-a]pyridin-2-yl]cyclopropanecarboxylic acid (10 mg, 27 μmol), (1S)-1-methylpropanol (10 μL, 108 μmol), DMAP (6.7 mg, 54 μmol) and EDCI.HCl (10.5 mg, 54 μmol) in DCM (0.5 mL) was stirred in a sealed vial at RT overnight before more (1S)-1-methylpropanol (10 μL, 108 μmol) and DMAP (6.7 mg, 54 μmol) was added and the mixture was heated to 50° C. for 3 hours. Evaporated to dryness and acidic prepHPLC purification afforded the title compound. HPLC-Retention time (XE Metode 7 CM): 2.35 minutes. Detected "M+1"-mass: 422.16. Calculated "M+1"-mass: 422.17. $^1$H NMR (DMSO, 600 MHz): δ=8.25-8.21 (m, 1H), 8.14 (dd, 1H, J=8.0, 1.2 Hz), 8.01-7.97 (m, 1H), 7.41 (d, 1H, J=8.2 Hz), 7.23 (d, 1H, J=8.2 Hz), 5.51 (s, 2H), 4.78 (h, 1H, J=6.3 Hz), 4.04 (s, 3H), 1.61-1.40 (m, 6H), 1.13 (d, 3H, J=6.2 Hz), 0.78 (t, 3H, J=7.4 Hz) ppm.

Example 2

[(1R)-1-Methylpropyl]1-[8-methoxy-5-(1-oxo-3H-isobenzofuran-5-yl)-[1,2,4]triazolo-[1,5-a]pyridin-2-yl]cyclopropanecarboxylate (Compound 2)

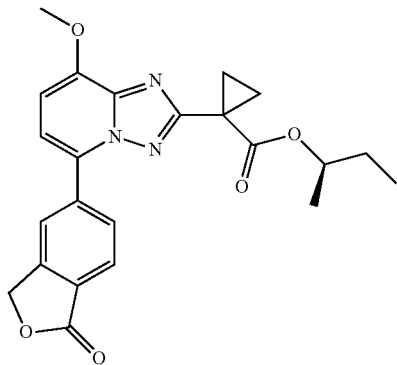 [SMILES: CC[C@@H](C)OC(=O)C1(c2nc3c(OC)ccc(-c4ccc5c(c4)COC5=O)n3n2)CC1]

A mixture of 1-[8-methoxy-5-(1-oxo-3H-isobenzofuran-5-yl)-[1,2,4]triazolo[1,5-a]pyridin-2-yl]cyclopropanecarboxylic acid (400 mg, 1.095 mmol), (2R)-butan-2-ol (122 mg, 1.64 mmol), DMAP (147 mg, 1.20 mmol) and EDCI.HCl (231 mg, 1.20 mmol) in DCM (10 mL) was stirred at RT overnight before it was evaporated to dryness. Column chromatography (gradient MeOH 0 to 5% in DCM) followed by recrystallization in EtOH and freeze drying afforded the title compound as colorless powder (138 mg, 30%). HPLC-Retention time (XE Metode 7 CM): 2.33 minutes. Detected "M+1"-mass: 422.15. Calculated "M+1"-mass: 422.17. $^1$H NMR (DMSO, 400 MHz): δ=8.23 (br s, 1H), 8.14 (dd, 1H, J=8.0, 1.6 Hz), 7.99 (d, 1H, J=8.0 Hz), 7.41 (d, 1H, J=8.2 Hz), 7.24 (d, 1H, J=8.2 Hz), 5.51 (s, 2H), 4.78 (h, 1H, J=6.3 Hz), 4.04 (s, 3H), 1.62-1.38 (m, 6H), 1.13 (d, 3H, J=6.3 Hz), 0.78 (t, 3H, J=7.4 Hz) ppm.

Example 3

[2-Methylpropyl]1-[8-methoxy-5-(1-oxo-3H-isobenzofuran-5-yl)-[1,2,4]triazolo[1,5-a]pyridin-2-yl]cyclopropanecarboxylate (Compound 3)

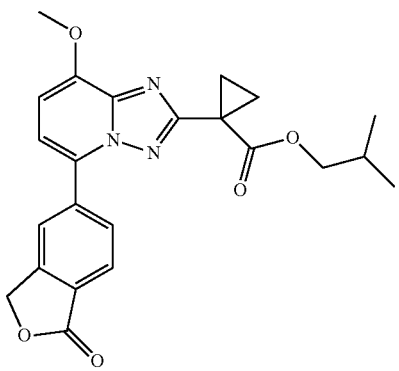 [SMILES: COc1ccc(-c2ccc3c(c2)COC3=O)n2nc(C3(C(=O)OCC(C)C)CC3)nc12]

A mixture of 1-[8-methoxy-5-(1-oxo-3H-isobenzofuran-5-yl)-[1,2,4]triazolo[1,5-a]pyridin-2-yl]cyclopropanecarboxylic acid (250 mg, 685 μmol), isobutanol (100 μL, 1.37 mmol), DMAP (250 mg, 2.05 mmol) and EDCI.HCl (262 mg, 1.37 mmol) in DCM (14 mL) was stirred at 50° C. for 2 hours in a sealed vial, before it was diluted with DCM (80 mL), washed with an aqueous 1 M solution of HCl (40 mL) and evaporated to dryness. The crude mixture was redissolved in MeCN (~2 mL) and the crude product was crystallized upon addition of water (~2 mL). Column chromatography (gradient EtOAc 20 to 100% in pet. ether) and subsequent recrystallization in MeCN and water afforded the title compound as colorless crystals (178 mg, 62%). HPLC-Retention time (XE Metode 7 CM): 2.34 minutes. Detected "M+1"-mass: 422.16. Calculated "M+1"-mass: 422.17. $^1$H NMR (DMSO, 600 MHz): δ=8.22 (br s, 1H), 8.13 (dd, 1H, J=8.1 Hz, 1.5 Hz), 8.00 (d, 1H, J=8.0 Hz), 7.40 (d, 1H, J=8.2 Hz), 7.24 (d, 1H, J=8.2 Hz), 5.51 (s, 2H), 4.04 (s, 3H), 3.84 (d, 2H, J=6.5 Hz), 1.79 (m, 1H), 1.61-1.54 (m, 2H), 1.54-1.46 (m, 2H), 0.78 (d, 6H, J=6.7 Hz) ppm.

Example 4

Tert-butyl 1-[8-methoxy-5-(1-oxo-3H-isobenzofuran-5-yl)-[1,2,4]triazolo[1,5-a]pyridin-2-yl]cyclopropanecarboxylate (Compound 4)

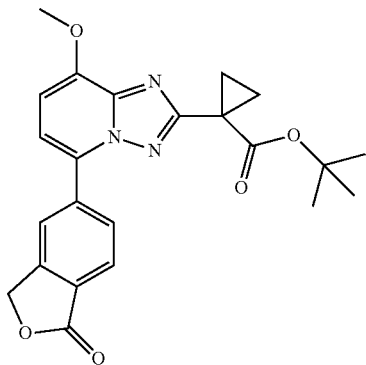 [SMILES: COc1ccc(-c2ccc3c(c2)COC3=O)n2nc(C3(C(=O)OC(C)(C)C)CC3)nc12]

A suspension of 1-[8-methoxy-5-(1-oxo-3H-isobenzofuran-5-yl)-[1,2,4]triazolo[1,5-a]pyridin-2-yl]cyclopropanecarboxylic acid (30 mg, 83 µmol) and benzyltriethyl-ammonium chloride (19 mg, 83 µmol) in DMF (1.0 mL) was gently heated until it became a solution. Tert-butyl bromide (297 µL, 2.64 mmol) and $K_2CO_3$ (171 mg, 1.24 mmol) were added and the mixture was stirred at 55° C. for three days. Additional tert-butyl bromide (139 µL, 1.24 mmol) and $K_2CO_3$ (171 mg, 1.24 mmol) were added and the mixture was stirred at 55° C. for one more day. PrepHPLC purification afforded the title compound. HPLC-Retention time (XE Metode 7 CM): 2.29 minutes. Detected "M+1"-mass: 422.18. Calculated "M+1"-mass: 422.17. $^1$H NMR (DMSO, 300 MHz): δ=8.27-8.22 (m, 1H), 8.16 (dd, 1H, 3=8.0, 1.5 Hz), 8.00 (d, 1H, J=8.2 Hz), 7.40 (d, 1H, J=8.2 Hz), 7.22 (d, 1H, J=8.3 Hz), 5.51 (s, 2H), 4.04 (s, 3H), 1.54-1.40 (m, 4H), 1.38 (s, 9H) ppm.

Assays

PDE4 Assay

Human recombinant PDE4 (Genbank accession no NM_006203) was incubated for 1 hour with the test compound at concentrations up to 10 µM, with cAMP (1×10-5M), and with a low amount (0.021 MBq) of radioactively labelled cAMP. At the end of the incubation, the cleavage of the substrate was evaluated by the binding of the AMP product to SPA beads, which generate chemoluminescence when bound to the radioactive tracer. The AMP product inhibited the binding of the radioactive tracer to the beads, and the luminescent signal was competed.

The results were calculated as the molar concentrations resulting in 50% inhibition of the substrate cleavage compared to controls samples, and are expressed as a range of $IC_{50}$ (nM).

The compounds of the present invention were tested in the PDE4 assay, $IC_{50}$ (nM): Compound 1, 10.6 nM; Compound 2, 13.0 nM; Compound 3, 12.3 nM; Compound 4, 20.7 nM (based on an average value of from 2 to 5 tests for each compound).

TNF-α Release

Human peripheral blood mononuclear cells (PBMC) were isolated from buffy coats. The blood is mixed with saline at a ratio of 1:1, and the PBMC were isolated using Lymphoprep Tubes™ (Nycomed, Norway). The PBMC were suspended in RPMI1640 with 0.5% human serum albumin, pen/strep and 2 mM L-glutamine at a concentration of 5×105 c/ml. The cells were pre-incubated for 30 minutes with the test compounds in 96 well tissue culture plates and stimulated for 18 hours with lipopolysaccharide 1 mg/ml (Sigma). TNF-α concentration in the supernatants was measured using homogeneous time-resolved fluorescence resonance (TR-FRET). The assay is quantified by measuring fluorescence at 665 nm (proportional to TNF-a concentration) and 620 nm (control).

Results are expressed as $IC_{50}$ values (nM) calculated from inhibition curves using as positive controls the secretion in LPS stimulated wells and as negative controls the secretion in unstimulated cells.

The compounds of the present invention were tested in the TNF-α release assay, $IC_{50}$ (nM): Compound 1, 12.8 nM; Compound 2, 15.7 nM; Compound 3, 14.6 nM; Compound 4, 15.3 nM (based on an average value of from 2 to 5 tests for each compound).

HLM (Human Liver Microsomes) Assay

Incubations of test compounds in DMSO, diluted with phosphate buffer, pH 7.4, at 0.5 µM were carried out with human liver microsomes (0.5 mg/mL). The percentage of organic solvent in the incubations was 1%. The human liver microsomal suspension in phosphate buffer was mixed with NADPH (1 mM) and preheated to 37° C. before test compound was added. Aliquots were taken at 0, 5, 10, 20 and 30 minutes, and reactions were terminated by addition of methanol containing analytical internal standard (IS).

The results were expressed as apparent clearance ($Cl_{app}$) (mL/min/kg) and hepatic extraction ratio ($E_h$) (%) calculated from the rate constant (k) (min$^{-1}$) of test compound depletion.

The compounds of the present invention were tested in the HLM assay, $E_h$ (%): Compound 1, >91%; Compound 2, >91%; Compound 3, >91%; Compound 4, >91% (based on an average value of from 2 to 3 tests for each compound).

Human Whole Blood (WB) Assay

Incubations of test compounds in DMSO, diluted with phosphate buffer, pH 7.4, at 1 µM were carried out with human whole blood. The percentage of organic solvent in the incubations was 1%. The incubations were performed at 37° C. with aliquots taken at 0, 15, 30, 60 and 120 minutes, and reactions were terminated by addition of methanol containing analytical internal standard (IS).

The results were expressed as half-life (T½) in minutes calculated from the rate constant (k) (min$^{-1}$) of test compound depletion.

The examples of the present invention were tested in the WB assay, T½ (minutes): Compound 1, 10.7 minutes; Compound 2, 12.6 minutes; Compound 3, 16.6 minutes; Compound 4, <11.2 minutes (based on an average value of from 2 to 4 tests for each compound).

Keratinocyte Stability (KC) Assay

Incubations of test compounds in DMSO, diluted with growing medium, pH ~7.4, at 1 µM were carried out with plated human keratinocytes. The percentage of organic solvent in the incubations was 0.5%. The incubations were performed at 37° C. with aliquots taken at 0, 60, 120, 240 and 1440 minutes, and reactions were terminated by addition of methanol containing analytical internal standard (IS).

The results were expressed as half-life (T½) in minutes calculated from the rate constant (k) (min$^{-1}$) of test compound depletion.

The examples of the present invention were tested in the KC assay, T½ (minutes): Compound 1, >720 minutes; Compound 2, >720 minutes; Compound 3, >720 minutes; Compound 4, >720 minutes (based on an average value of from 2 to 4 tests for each compound).

The invention claimed is:

1. A method of treating dermal diseases or conditions, which method comprises the step of administering to person suffering from said disease or condition a therapeutically effective amount of tert-butyl 1-[8-methoxy-5-(1-oxo-3H-isobenzofuran-5-yl)-[1,2,4]triazolo[1,5-a]pyridin-2-yl]cyclopropanecarboxylate, optionally together with a pharmaceutically acceptable carrier or one or more excipients, wherein the dermal disease or condition is selected from the group consisting of dermatitis, atopic dermatitis, seborrheic dermatitis, contact dermatitis, psoriasis, acne, pruritis, eczema, COPD and asthma.

* * * * *